US005786332A

United States Patent [19]

Girten et al.

[11] Patent Number: 5,786,332

[45] Date of Patent: Jul. 28, 1998

[54] CYTOKINE RESTRAINING AGENTS AND METHODS OF USE IN PATHOLOGIES AND CONDITIONS ASSOCIATED WITH ALTERED CYTOKINE LEVELS

[75] Inventors: Beverly E. Girten, San Diego; Richard A. Houghten, Del Mar; Costas C. Loullis, Cardiff; Mark J. Suto, San Diego; Ronald R. Tuttle, Escondido, all of Calif.

[73] Assignee: Trega Biosciences, Inc., San Diego, Calif.

[21] Appl. No.: 400,983

[22] Filed: Mar. 6, 1995

[51] Int. Cl.$^6$ .......... A61K 38/00

[52] U.S. Cl. .......... 514/16; 514/8; 514/17; 514/18; 530/317; 530/322; 530/329; 530/330; 530/331

[58] Field of Search .......... 514/8, 16, 17, 514/18; 530/317, 322, 329, 330, 331

[56] References Cited

U.S. PATENT DOCUMENTS

| | | | |
|---|---|---|---|
| 4,457,864 | 7/1984 | Hruby et al. | 260/112.5 |
| 4,485,039 | 11/1984 | Hruby et al. | 260/112.5 R |
| 4,649,191 | 3/1987 | Hruby | 530/329 |
| 4,866,038 | 9/1989 | Hruby et al. | 514/14 |
| 4,918,055 | 4/1990 | Hruby et al. | 514/14 |
| 5,028,592 | 7/1991 | Lipton | 514/18 |
| 5,049,547 | 9/1991 | Hruby et al. | 514/14 |
| 5,157,023 | 10/1992 | Lipton | 514/18 |
| 5,408,038 | 4/1995 | Smith et al. | 530/359 |
| 5,420,109 | 5/1995 | Suto et al. | 514/8 |
| 5,462,927 | 10/1995 | Moreau et al. | 514/17 |

FOREIGN PATENT DOCUMENTS

| | | |
|---|---|---|
| 0 292 291 | 5/1988 | European Pat. Off. . |
| 0 427 458 | 5/1991 | European Pat. Off. . |
| 0427458 | 5/1991 | European Pat. Off. . |
| 0 568 925 | 4/1993 | European Pat. Off. . |
| 2691465A1 | 11/1993 | France . |
| WO 87/04623 | 3/1987 | WIPO . |

OTHER PUBLICATIONS

Yajima et al., "Studies on peptides. XI. The effect on melanotropic activity of altering the arginyl residue in L–histidyl–L–phenylalanyl–L–arginyl–L–tryptophylglycine" *Biochim. Biophys. Acta*, 127:545–549 (1966).

Chemical abstract No. 16789n, p. 1613, vol. 66, No. 5, Jan. 30, 1967.

Abou–Mohamed et al., "HP–228, a novel synthetic peptide, inhibits the induction of nitric oxide synthase in vivo but no in vitro". *J. Pharmacol. Exp. Ther.*, Abstract No. 959276, 275(2) :584–591 (Jul. 21, 1995).

Mackensen et al., "Treatment of cancer patients with endotoxin induces release of endogenous cytokines." *Pathobiol.*, 59:264–267 (1991).

Mackensen et al., "Modulating activity of interferon–γ on endotoxin–induced cytokine production in cancer patients." *Blood*, 78(12):3254–3258 (1991).

Rabinowitz et al., "Characterization of endogenous cytokine concentrations after high–dose chemotherapy with autologous bone marrow support." *Blood*, 81(9) :2452–2459 (1993).

(List continued on next page.)

*Primary Examiner*—Cecilia J. Tsang
*Assistant Examiner*—C. Delacroix-Muirheid
*Attorney, Agent, or Firm*—Campbell & Flores LLP

[57] ABSTRACT

The present invention relates to novel peptides that are potent cytokine restraining agents. In addition, the present invention relates to pharmaceutical compositions comprising a pharmaceutically acceptable carrier and a cytokine restraining agent. Administration of such a cytokine restraining agent to a subject restrains, but does not necessarily suppress, cytokine activity completely. Thus, the present invention provides a method of restraining pathologically elevated cytokine activity in a subject. The invention also provides methods of treating disuse deconditioning and diseases mediated by nitric oxide and cytokines, such as diabetes and glomerulonephritis, a method of organ protection, a method of organ protection, and a method of reducing the negative side effects of cancer chemotherapy, such as nephrotoxicity.

46 Claims, 1 Drawing Sheet

OTHER PUBLICATIONS

Creekmore et al., "Strategies for clinical monitoring of therapeutic trials." *Manual of Clin. Lab. Immunol.*, 915–922 (1992).

Thavasu et al., "Measuring cytokine levels in blood: Importance of anticoagulans, processing, and storage conditions." *J. of Immunol. Methods*, 153:115–124 (1992).

Payne et al., "Hypothalamic releasing hormones mediating the effects of interleukin–1 on sleep." *J. of Cell. Biochem.*, 53:309–313 (1993).

Tilg et al., "Interleukin–6 (IL–6) as an Anti–inflammatory cytokine: induction of circulating IL–1 receptor antagonist and soluble tumor necrosis factor receptor p55." *Blood*, 83(1):113–118 (1994).

Wong et al., "Interleukin (IL) 4 differentially regulates monocyte IL–1 family gene expression and synthesis In Vitro and In Vivo." *J. Exp.Med.*, 177:775–781 (1993).

Gorgen et al., "Granulocyte colony–stimulating factor treatment protects rodents against lipopolysaccharide–induced toxicity via suppression of systemic tumor necrosis factor–α. " *J. of Immonol.*, 149:918–924 (1992).

Dinarello et al., "The role of interleukin–1 in disease." *New England J. Med.*, 328:106–113 (1993).

Richar and Lipton, "Effect of α–MSH 11–13 (Lysine–Proline–Valine) on Fever in the Rabbit." *Peptides*, 5:815–817 (1984).

Deeter et al., "Antipyretic properties of centrally administered α–MSH fragments in the rabbit." *Peptides*9:1285–1288 (1989).

Sugg et al., "D–Isomeric replacements within the 6–9 core sequence of a Ac–[$Nle^4$]–α–$MSH_{4-11}$–$NH_2$: A topological model for the solution conformation of α–Melanotropin." *Biopolymers*, 25:2029–2042 (1986).

Norlund, James J., "α–Melanocyte–stimulating hormone a ubiquious cytokine with pigmenting effects." *J. Amer. Med. Assoc.*, 226:2753–2754 (1991).

Levine et al., "Induction of skin tanning by subcutaneous administration of a potent synthetic melanotropin." *J. Amer. Med. Assoc.*, 266:2730–2736 (1991).

Al–Obeidi et al., "Design of a new class of superpotent cyclic α–melanotrophins based on quenched dynamic simulations." *J. Am. Chem. Soc.*, 111:3413–3416 (1989).

Poole et al., "Peripheral analgesic activities of peptides related to α–melanocyte stimulating hormone and interleukin–1$\beta^{193-195}$." *Br. J. Pharmacol.* 106:489–492 (1992).

Follenfant et al., "Inhibition by neuropeptides of interleukin–1 α–induced prostaglandin–independent hyperalgesia.", 98:41–43 (1989).

Rivier et al., "In the mouse, the activation of the hypothalamic–pituitary–adrenal axis by a lipopolysaccharide (Endotoxin) is mediated through interleukin–1." *Endocrinology*, 125(6) :2800–2805 (1989).

Vinegar et al., "Biphasic development of carrageenin edema in rats." *J. of Pharmacol and Exper. Therapeutics*, 166(1); 96–103 (1969).

Vinegar et al., "Pathway to carrageenan–induced inflammation in the hind limb of the rat." *Federation Proc.*, 46:118–126 (1987).

Hiltz and Lipton, "Alpha–MSH peptides inhibit acute inflammation and contact sensitivity." *Peptides*, 11(5) 979–982 (1990).

Ray et al., "Cytokines and their receptors: Molecular mechanism of interleukin–6 gene repression by glucocorticoids." *J. Am. Soc. Nephrol.*, 2:s214–s221 (1992).

Karkar et al., "Passive immunization against tumor necrosis factor–alpha (TNF–α) and IL–1βprotects from LPS enhancing glomerular injury in nephrotoxic nephritis in rats." *Clin. Exp. Immunol.*, 90:312–318 (1992).

Ulich et al., "Indotoxin–induced cytokine gene expression *in–vivo*". *Am. J. of Pathol.*, 141(1) :61–68 (1992).

Jansen et al., "Induction of nitric oxide synthase in rat immune complex glomerulonephritis." *Kidney Int'l.*, 45: 1215–1219 (1994).

Yajima et al., *Chem. Pharm. Bull.*, 15(4), 504–510. 1967.

Dayhoff, M. , *Atlas of Protein Sequence and Structure*, vol. 5, 1972, p. 96.

CYTOKINE RESTRAINING AGENTS AND METHODS OF USE IN PATHOLOGIES AND CONDITIONS ASSOCIATED WITH ALTERED CYTOKINE LEVELS

BACKGROUND OF THE INVENTION

FIELD OF THE INVENTION

The present invention relates generally to the fields of peptide chemistry and molecular pathology and, more specifically, to novel cytokine restraining agents and their use in disuse deconditioning, organ protection, cancer chemotherapy, diabetes, and glomerulonephritis.

BACKGROUND INFORMATION

Cytokines are a class of proteins produced by cells in response to variety of environmental, mechanical, and pathological stresses. For example, cytokines are produced in response to T cell stimulation during an immune response. The immune and acute phase responses associated with disuse deconditioning, organ transplant, cancer treatment, and diabetes are all associated with alterations in cytokine levels.

Cytokines are normally present in very low concentrations in a tissue and their effects are mediated through binding to high affinity receptors on specific cell types. Various cytokines such as the interleukins (IL), interferons (IF) and tumor necrosis factor (TNF) are produced during immune, inflammatory, and acute phase responses and control various aspects of these responses. Following induction of such an immune, inflammatory, or acute phase response, the concentrations of the various cytokines increase at different times. For example, increased levels of cytokines are associated with a variety of situations that lead to disuse deconditioning, such as space flight, immobilization, spinal cord injury, and bed rest. With space flight, for example, TNF, IL-6, and IL-2 levels increase upon a subject's initial exposure to space and again upon return from space. Altered levels of cytokines have also been linked to abnormal bone metabolism and rapid decalcification that occurs during immobilization, spinal cord injury, and long-term bed rest. Cytokine levels are similarly increased during such chronic pathological states as organ transplant, nephrotoxicity associated with the administration of cyclosporine to transplant subjects, chemotherapy of cancer patients, diabetes, and glomerulonephritis.

TNF, IL-1, IL-6 and IL-8 mediate host defense responses, cell regulation and cell differentiation. For example, these cytokines can induce fever in a subject, cause activation of T and B cells and affect the levels of other cytokines, which result in a cascade effect whereby other cytokines mediate the biological action of the first cytokine.

Cytokines have multiple biological activities and interact with more than one cell type. In addition, some cells interact with more than one type of cytokine. As a result, it has not been possible to prevent damage by targeting only one particular cytokine or cell type. A better approach for preventing damage due to cytokines would be to restrain the expression of all or several of the cytokines involved in a response, without eliminating expression of any one cytokine in its entirety. In this way, complete immunosuppression can be prevented and homeostasis can be maintained.

Corticosteroids effectively modulate cytokine expression. However, corticosteroids can cause complete immunosuppression and have other undesirable side effects such as inducing "wasting" syndrome, diabetes and osteoporosis. Non-steroidal anti-inflammatory drugs (NSAID) such as ketorolac (Toradol®; Syntex) also are effective in treating inflammation and pain. However, these drugs act by inhibiting prostaglandin production, which can lead to potentially severe complications including gastric ulceration, bleeding and renal failure.

In order to prevent pathological conditions, caused by the expression of cytokines, such as those described above, it would be advantageous if cytokine levels could be readily controlled in a tissue. However, modifying the physiologic effect of cytokines has been hindered due to their pleiotropic effects. Thus, a need exists for agents that can restrain the activity of cytokines in a subject without causing undesirable side effects. Further, a need exists for identifying agents which can be used in the treatment of pathologies and conditions associated with altered cytokine levels, such as, disuse deconditioning, organ protection, cancer chemotherapy, diabetes and glomerulonephritis. The present invention satisfies these needs and provides related advantages as well.

SUMMARY OF THE INVENTION

The present invention relates to novel peptides that are potent cytokine restraining agents. Novel cytokine restraining peptides having the general structures, $X_1$-$X_2$-His-(D)Phe-Arg-(D)Trp-$X_3$ and $X_4$-$X_5$-(D)Phe-Arg-(D)Trp-$X_3$, where $X_1$, $X_2$, $X_3$, $X_4$, and $X_5$ can be amino acids or amino acid analogs, are disclosed. The invention also relates to a cytokine restraining peptide having the structure, Ac-His-(D)Phe-Arg-(D)Trp($CH_2$)-((NAc)Gly-$NH_2$, which contains a reduced (D)Trp analog.

In addition, the present invention relates to pharmaceutical compositions comprising a pharmaceutically acceptable carrier and a cytokine restraining agent. Administration of such a cytokine restraining agent to a subject restrains, but does not necessarily suppress, cytokine activity completely. Thus, the present invention provides a method of restraining pathologically elevated cytokine activity in a subject. The invention also provides methods of treating disuse deconditioning and diseases mediated by nitric oxide and cytokines, such as diabetes and glomerulonephritis, a method of organ protection, and a method of reducing the negative side effects of cancer chemotherapy, such as nephrotoxicity.

DETAILED DESCRIPTION OF THE INVENTION

Figure 1A:
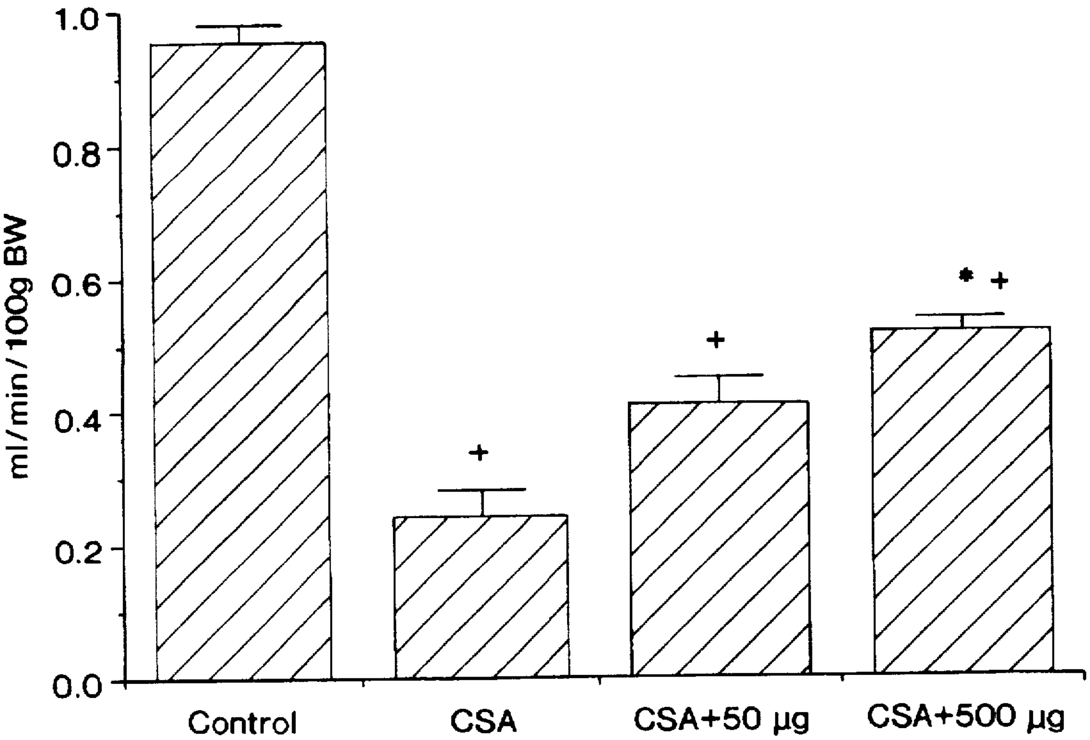
FIGS. 1*a* and *b* show the effect of a cytokine restraining agent on glomerular filtration rate of cyclosporine-induced nephrotoxicity.

The present invention generally relates to novel cytokine restraining agents having the structure: $X_1$-$X_2$-His -(D)Phe-Arg-(D)Trp-$X_3$, wherein $X_1$ is 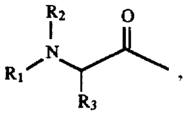 , H or $COCH_3$;

-continued $X_2$ is 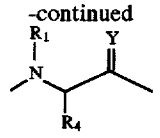 ; and $X_3$ is 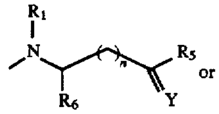 or $R_5$;

$R_1$ is H, $COCH_3$, $C_2H_5$, $CH_2Ph$, COPh, COO-t-butyl, $COOCH_2Ph$, $CH_2CO$-(polyethylene glycol) or A; $R_2$ is H or $COCH_3$; $R_3$ is a linear or branched alkyl group having 1 to 6 carbon atoms or a cyclic alkyl group having 3 to 6 carbon atoms; $R_4$ is $(CH_2)_m$—$CONH_2$, $(CH_2)_m$—$CONHR_1$, or $(CH_2)_m$—CONHA; $R_5$ is OH, $OR_3$, $NH_2$, SH, $NHCH_3$, $NHCH_2Ph$ or A; and $R_6$ is H or $R_3$; and wherein "Ph" is $C_6H_5$, "m" is 1, 2 or 3, "n" is 0, 1, 2 or 3, and "A" is a carbohydrate having the general formula:

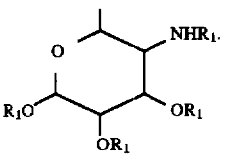

In one embodiment of the present invention, the peptides have any of the variables described above for $X_1$ and $X_2$ and specifically have OH for $X_3$ ($X_3$ is $R_5$, wherein $R_5$ is OH). In yet another embodiment, Y, $R_1$, $R_2$, $R_4$, $R_5$, and $R_6$ can be any of the variables described above and $R_3$ is a cyclic alkyl group having 3 to 6 carbon atoms.

Exemplary peptides encompassed by the formulas described above which are provided by the present invention include Nle-Gln-His-(D)Phe-Arg-(D)Trp-Gly-$NH_2$; Ac-Nle-Gln-His-(D)Phe-Arg-(D)Trp-Gly-$NH_2$; and Ac-(cyclohexyl)Gly-Gln-His-(D)Phe-Arg-(D)Trp-Gly-$NH_2$, each of which can restrain cytokine activity.

The present invention also relates to novel cytokine restraining agents having the structure: $X_4$-$X_5$-(D)Phe-Arg-(D)Trp-$X_3$, wherein $X_4$ is 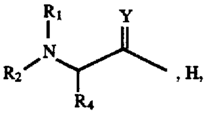 , H, $COCH_3$, $X_3$ is 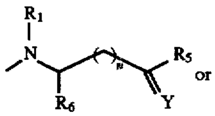 or $R_5$;

$R_1$ is H, $COCH_3$, $C_2H_5$, $CH_2Ph$, COPh, COO-t-butyl, $COOCH_2Ph$, $CH_2CO$-(polyethylene glycol) or A; $R_2$ is H or $COCH_3$; $R_3$ is a linear or branched alkyl group having 1 to 6 carbon atoms or a cyclic alkyl group having 3 to 6 carbon atoms; $R_4$ is $(CH_2)_m$—$CONH_2$, $(CH_2)_m$—$CONHR_1$, or $(CH_2)_m$—CONHA; $R_5$ is OH, $OR_3$, $NH_2$, SH, $NHCH_3$, $NHCH_2Ph$ or A; and $R_6$ is H or $R_3$; and wherein "Ph" is $C_6H_5$, "m" is 1, 2 or 3, "n" is 0, 1, 2 or 3, and "A" is a carbohydrate having the general formula

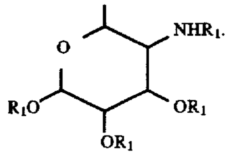

In one embodiment of the present invention, the peptides are shortened analogs of 3 to 5 amino acid residues, having any of the variables described above for $X_4$ and $X_5$ and specifically having OH for $X_3$ ($X_3$ is $R_5$, wherein $R_5$ is OH). In yet another embodiment, where $X_4$ is absent, $X_5$ is H or $COCH_3$, and $X_3$ is $R_5$, the cytokine restraining agents are tripeptides of (D)Phe-Arg-(D)Trp. Preferred peptides include His-(D)Phe-Arg-(D)Trp-Gly-$NH_2$; Ac-His-(D)Phe-Arg-(D)Trp-$NH_2$; His-(D)Phe-Arg-(D)Trp-OH; Ac-(D)Phe-Arg-Trp-$NH_2$; and cyclo(His-(D)Phe-Arg-(D)Trp), which can restrain cytokine activity.

As used herein, the term "restrain" has its commonly understood meaning, i.e., to limit, restrict, keep under control or moderate. It follows that a "cytokine restraining agent" is an agent that has an action that limits or controls the biological activity of a cytokine. A cytokine restraining agent can be, for example, a peptide comprising amino acids or amino acid analogs as described herein. In addition to the examples provided above, other representative examples of peptide cytokine restraining agents include:

1) Ac-Nle-Gln-His-(D)Phe-Arg-(D)Trp-Gly-OH;
2) Ac-Nle-Gln-His-(D)Phe-Arg-(D)Trp-Gly-$NH_2$;
3) Ac-Nle-Gln-His-(D)Phe-Arg-(D)Trp-Gly-$OC_2H_5$;
4) Ac-Nle-Gln-His-(D)Phe-Arg-(D)Trp-Gly-NH-$NH_2$;
5) Ac-Nle-Asn-His-(D)Phe-Arg-(D)Trp-Gly-$NH_2$;
6) Ac-Nle-Asn-His-(D)Phe-Arg-(D)Trp-Gly-OH;
7) Ac-Nle-Gln-His-(D)Phe-Arg-(D)Trp-Gly-$NHCH_2CH_2Ph$;
8) Ac-Nle-Gln-His-(D)Phe-Arg-(D)Trp-Gly-$NHCH_2Ph$;
9) 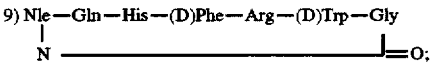 ;
10) Ac-Gln-His-(D)Phe-Arg-(D)Trp-Gly-$NH_2$;
11) Ac-Nle-Gln-His-(D)Phe-Arg-(D)Trp-$NH_2$;
12) Ac-His-(D)Phe-Arg-(D)Trp-Gly-$NH_2$;
13) His-(D)Phe-Arg-(D)Trp-$NH_2$;
14) Ac-His-(D)Phe-Arg-(D)Trp-OH; and
15) Ac-His-(D)Phe-Arg-(D)Trp($CH_2$)-(NAc)Gly-$NH_2$, wherein (D)Trp($CH_2$) is an analog of (D)Trp, where $H_2$ replaces the α-carbonyl oxygen and (NAc)Gly is a glycine derivative with an N-acetyl moiety.

Peptide cytokine restraining agents as described above are characterized, in part, by a core structure having the amino acid sequence, (D)Phe-Arg-(D)Trp, or an analog of (D)Trp, and more preferably the core amino acid sequence His-(D)Phe-Arg-(D)Trp, or an analog of (D)Trp. The amino acids are indicated by their commonly known three letter code and (D) designates an amino acid having the "D" configuration, as opposed to the naturally occurring L-amino acids. Where no specific configuration is indicated, one skilled in the art would understand the amino acid to be an (L)-amino acid. In the peptides exemplified above, "Nle" is the three letter code for norleucine and "Ph" indicates a "phenyl" group ($C_6H_5$).

Cytokine restraining agents such as the peptides described above were synthesized using a modification of the solid phase peptide synthesis method of Merrifield (*J. Am. Chem. Soc.*, 85:2149 (1964), which is incorporated herein by reference) or can be synthesized using standard solution methods well known in the art (see, for example, Bodanzsky, M., *Principles of Pentide Synthesis* 2nd revised ed. (Springer-Verlag, 1988 and 1993), which is incorporated herein by reference). Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:5131 (1985), which is incorporated herein by reference.

Peptides were synthesized using amino acids or amino acid analogs, the active groups of which were protected as necessary using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

One skilled in the art would know that the choice of amino acids or amino acid analogs incorporated into the peptide will depend, in part, on the specific physical, chemical or biological characteristics required of the cytokine restraining peptide. Such characteristics are determined, in part, by the route by which the cytokine restraining agent will be administered or the location in a subject to which the cytokine restraining agent will be directed.

Selective modification of the reactive groups in a peptide also can impart desirable characteristics to a cytokine restraining agent. Peptides can be manipulated while still attached to the resin to obtain N-terminal modified compounds such as an acetylated peptide or can be removed from the resin using hydrogen fluoride or an equivalent cleaving reagent and then modified. Compounds synthesized containing the C-terminal carboxyl group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus or methods for amidation of the C-terminus. Similarly, methods for modifying side chains of the amino acids or amino acid analogs are well known to those skilled in the art of peptide synthesis. The choice of modifications made to the reactive groups present on the peptide will be determined by the characteristics that the skilled artisan requires in the peptide.

Particular cyclic peptides also can be an effective cytokine restraining agent. A cyclic peptide can be obtained by inducing the formation of a covalent bond between, for example, the amino group at the N-terminus of the peptide and the carboxyl group at the C-terminus. For example, the peptide, cyclo(His-(D)Phe-Arg-(D)Trp), which can be produced by inducing the formation of a covalent bond between His and (D)Trp, can have cytokine restraining activity. Alternatively, a cyclic peptide can be obtained by forming a covalent bond between a terminal reactive group and a reactive amino acid side chain or between two reactive amino acid side chains. One skilled in the art would know that the choice of a particular cyclic peptide is determined by the reactive groups present on the peptide as well as the desired characteristic of the peptide. For example, a cyclic peptide may provide a cytokine restraining agent with increased stability in vivo.

A newly synthesized peptide can be purified using a method such as reverse phase high performance liquid chromatography (RP-HPLC), which is described in detail below (see Example I), or other methods of separation based on the size or charge of the peptide. Furthermore, the purified peptide can be characterized using these and other well known methods such as amino acid analysis and mass spectrometry, which are described in detail below (see Example I).

The invention also relates to pharmaceutical compositions comprising a cytokine restraining agent and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters.

A pharmaceutically acceptable carrier can contain physiologically acceptable compounds that act, for example, to stabilize the cytokine restraining agent or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the cytokine restraining agent and on the particular physio-chemical characteristics of the specific cytokine restraining agent.

A cytokine restraining peptide as described above or a pharmaceutical composition containing a cytokine restraining agent can be administered to a subject in order to restrain pathologically elevated cytokine activity in the subject. For example, the peptide or composition can be administered to a subject as a treatment for inflammation, pain, cachexia, adult respiratory distress syndrome, and pathoimmunogenic diseases such as arthritis, inflammatory bowel disease and systemic lupus erythematosus, each of which is characterized by pathologically elevated cytokine activity.

As used herein, the term "pathologically elevated" means that a cytokine activity is elevated above a range of activities which is expected in a normal population of such subjects. For example, a normal range of IL-1 activity present in a specific tissue can be determined by sampling a number of subjects in the population. A subject having a pathology characterized by cytokine-induced pathological effects can be readily identified by determining that the cytokine activity in the subject is pathologically elevated, which is above the normal range.

In addition, as described in more detail below, the peptides or pharmaceutical compositions can also be used for treating disuse deconditioning and diseases mediated by nitric oxide, such as diabetes and glomerulonephritis, as well as for reducing the negative effects of a cancer chemotherapeutic agent, and for protecting organs against damage, all of which are associated with pathologically altered levels of cytokines.

Disuse Deconditioning

Altered levels of cytokines are associated with a variety of conditions that lead to disuse deconditioning, such as space flight, immobilization, spinal cord injury, bed rest, and trauma. Examples of other conditions which result in disuse deconditioning include, for instance, simulated weightlessness, casting, and denervation.

Space flight, for example, alters many immune responses and regulatory components of the immune response, including the cytokine network. Space flight, as well as model systems of space flight, affect the production and activation of various cytokines including interleukins and TNF. Levels of IL-6 and IL-2 are elevated on the first day of space flight and again after returning from space flight.

Cytokines also modulate the function of osteoclasts, and IL-1 and TNF have been implicated in the rapid decalcification or loss of bone mineral density that results from immobilization, bed rest and spinal cord injury. Correlation between cytokine expression and increased retrograde transport following injury suggests that cytokines play a role in peripheral nerve damage. Bed rest, when combined with intra-articular administration of steroids, produces a particularly rapid systemic effect on the acute phase response that is mediated by cytokines.

A cytokine restraining peptide of the present invention or a composition containing the peptide can be used for treating disuse deconditioning by reducing or ameliorating the negative effects of disuse deconditioning associated with altered cytokine levels. The negative effects include, for example, loss of muscle mass, bone density, exercise capacity, and oxygen consumption as well as decreased levels of oxidative and antioxidant enzymes, such as soleus citrate synthase, in muscle tissue.

Organ Protection

Cytokines also play an important role in organ damage and organ protection. For example, cytokines significantly affect such events and conditions as organ transplant, particularly the rejection of a transplanted organ, ischemia-reperfusion, cyclosporine-induced nephrotoxicity, myocardial infarction, and stroke.

Regarding organ transplant, cytokines, especially TNF, are important mediators of allograft rejection. Elevated serum levels of TNF occur in patients undergoing renal, hepatic, and cardiac allograft rejection. Further evidence of TNF presence has been demonstrated in rejecting rat cardiac and renal allografts as well as human renal and hepatic grafts. Acute rejection episodes in renal transplant patients are accompanied by an increase in serum IL-6 levels. The administration of glucocorticoids during such episodes was reported by Ray et al., *J. Am. Soc. Nephro.* 2(12):5214–5221 (1992), to lead to a rapid and marked decrease in IL-6 levels and the severity of the rejection episodes. The cytokine restraining agents of the present invention can be similarly useful in reducing the severity of such rejection episodes and the damage caused thereby.

Administration of immunosuppressive agents, such as cyclosporine, to transplant subjects also effects cytokine activity, causing cyclosporine-induced nephrotoxicity resulting in damage to the kidney. Agents which restrain cytokines, such as those of the present invention, can be effective in reducing cyclosporine-induced nephrotoxicity.

In addition, cytokine restraining agents of the present invention can protect against organ damage associated with ischemia-reperfusion, including such damage as decreased glomerular filtration rate and increased vascular resistance in the kidney. Ischemia-reperfusion injury has also been associated with elevations of cytokines. IL-1 and TNF mediate myocardial ischemia and increased levels of IL-1 can occur during the reperfusion phase of skeletal muscle ischemia. Increased TNF release follows both moderate and severe ischemic injury to the liver.

Thus, the present invention provides a method of protecting an organ of a subject against organ damage by administering a cytokine restraining peptide to the subject. The organ damage to be protected against can be the result of such conditions or events as an organ transplant, the administration of an immunosuppressive agent, such as cyclosporine, the resulting damage from ischemia-reperfusion, myocardial infarction, stroke, and the like.

As used herein "damage" includes damage to a whole organ, such as the dysfunctioning of an organ, or damage to a tissue of the organ. In many instances, damage to an organ or tissue involves, not only increased cytokine levels, but also increases in free radicals. For example, the activated white blood cells that result from ischemia release oxygen radicals and deliver aggressive mediators such as cytokines, which are chemotactic for leukocytes. This results in a cycle in which oxygen radicals and mediators, such as cytokines, are responsible for the augmentation of post-ischemic tissue or organ damage.

The type of damage which free radicals or cytokines can induce includes, but is not limited to, inflammation, increases in vascular permeability, fibrosis, and necrosis. These and other types of damage can be assessed histomorphologically by methods well known in the art. Damage also can be evidenced by organ dysfunction that is often reflected by changes in physiological and biochemical parameters which tend to be specific to a particular organ or tissue and which can be routinely measured by techniques well known in the art. For example, kidney dysfunction, indicative of renal damage, might lead to decreases in glomerular filtration rate and renal blood flow as well as increased renal vascular resistance. Examples of biochemical parameters that can be used as early markers of tissue and organ damage include increased nitric oxide or malondialdehyde levels. Malondialdehyde is a byproduct of lipid peroxidation and therefore indicative of free radical levels. Alternatively, or in addition thereto, increased levels of such enzymes as lactate dehydrogenase, a marker of cell death, can be assessed.

Organs which can be protected against damage by administration of the cytokine restraining agents of the present invention include, but are not limited to, the heart, kidney, liver, lung, brain, muscle, skin, or bone. An example of tissue within an organ which can be protected by the present invention is the epithelium in skin. Also included are organs which can be transplanted or which are associated with the negative side effects caused by the administration of an immunosuppressive agent to a transplant subject, as well as organs subject to ischemia-reperfusion, infarction, stroke, or other specific conditions or events which might lead to cellular damage or death. More than one organ may be protected at a time.

Cancer Chemotherapy

A cytokine restraining peptide of the present invention, or composition containing the peptide, can also be used in cancer chemotherapy for reducing the nephrotoxic effect or other negative effects of cancer chemotherapeutic agents. Cancer chemotherapeutic agents, such as cisplatin, Taxol® and Adriamycin®, induce and enhance the production of cytokines. Taxol®, a microtubule-stabilizing anti-neoplastic agent, induces expression of TNF and IL-1 and enhances the production of TNF in macrophages. Increased concentrations of IL-6 and TNF occur in patients receiving cisplatin, with cytokine concentrations being particularly elevated in patients experiencing renal or hepatic toxicity. Cytokine production is also increased in cancer patients during chemohyperthermia. TNF and IL-6 levels measured when a heating solution containing cisplatin is administered showed a dramatic increase in IL-6 occurring within 30 mn after the treatment started. TNF values were only slightly elevated.

As shown in the Examples, use of a present cytokine restraining peptide in cancer chemotherapy can reduce the nephrotoxic effect of a cancer chemotherapeutic agent. As well, the peptides can be administered to a subject undergoing cancer chemotherapy to reduce other negative side effects of chemotherapeutic drugs, including but not limited to, nausea, vomiting, mucositis, anorexia, fatigue, and organ dysfunction.

Diseases Mediated By Nitric Oxide and Cytokines, Including Diabetes and Glomerulonephritis Cytokines and nitric oxide (NO) are both important mediators of a variety of disease states, including, for example, diabetes and glomerulonephritis. Cytokines and NO regulate beta-cell damage in early insulin-dependent diabetes mellitus. IL-1, interferon gamma (IFN-G) and TNF induce islet NO. In parallel with NO production, IL-1, IFN-G, and TNF impair islet function, decrease glucose levels and decrease glucose-induced insulin release. Most of the deleterious effects caused by cytokines on islet cells can be prevented by blocking NO production. Although some studies have shown that isolated human islets are more resistant to the suppressive effects of cytokines and NO than isolated rodent islets, cytokines can suppress human islet function irrespective of their effects on NO generation.

Cytokines and NO also influence the degree of injury resulting from glomerulonephritis. TNF and IL-1 can increase the severity of glomerular injury in nephritis and, therefore, may be important in modulating glomerular injury clinically. Karker et al., *Clinical and Exp. Immunol.* 90(2): 312–318 (1992) have reported that agents which suppress cytokines are effective in reducing elevated albumin levels and tissue damage in glomerulonephritis. Other research has demonstrated that in vivo induction of inducible nitric oxide synthase (INOS) occurs in immune complex glomerulonephritis (Jansen et al., *Kidney International* 45(4):1215–1219, (1994)).

Cytokine restraining peptides of the present invention can be used for treating a subject having a disease mediated by nitric oxide and cytokines, such as diabetes and glomerulonephritis. As used herein, the term "treating" means reducing or alleviating one or more symptoms or conditions associated with a particular disease state mediated by NO and cytokines. For example, treating diabetes can be manifested by reducing glucose levels of a diabetic.

Cytokine restraining peptides or pharmaceutical compositions containing the peptides can be used for treating any of the above-described pathologies and conditions. One skilled in the art would know that a pharmaceutical composition comprising a cytokine restraining agent can be administered to a subject having elevated cytokine activity by various routes including, for example, orally, intra vaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment or powder, or active, for example, using a nasal spray or inhalant. A cytokine restraining agent also can be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

Cytokines can be expressed locally, such as at a site of localized infection, or can be expressed systemically, for example, as in disuse deconditioning or in an immune response. Cytokine expression can induce pyrexia (fever) and hyperalgesia (extreme sensitivity to pain) in a subject, as well as macrophage and monocyte activation, which produces or further contributes to an inflammatory response in a subject. Since cytokine expression can be localized or systemic, one skilled in the art would select a particular route and method of administration of the cytokine restraining agent based on the source and distribution of cytokines in a subject. For example, in a subject suffering from a systemic condition, such as disuse deconditioning, a pharmaceutical composition comprising a cytokine restraining agent can be administered intravenously, orally or by another method that distributes the cytokine restraining agent systemically. However, in a subject suffering from a pathology caused by localized cytokine expression, such as acute respiratory distress syndrome, a cytokine restraining agent can be suspended or dissolved in the appropriate pharmaceutically acceptable carrier and administered directly into the lungs using, for example, a nasal spray.

In order to restrain the biological activity of a cytokine, the cytokine restraining agent must be administered in an effective dose, which is about 0.0001 to 0.5 mg/kg body weight per injection, or by alternative modes of administration an effective does is about 0.0001 to 100 mg/kg body weight. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a cytokine restraining agent required to obtain an effective dose in a subject depends on many factors including the age and general health of the subject as well as the route of administration and the number of treatments to be administered. In view of these factors, the skilled artisan would adjust the particular dose so as to obtain an effective dose for restraining cytokine activity.

Examples of cytokine restraining agents and the effectiveness of a cytokine restraining agent in preventing or minimizing adverse biological effects mediated by cytokines are provided below and summarized in Tables I–V. As described below, cytokine restraining agents such as the peptides described in Example II can effectively restrain cytokine expression in mice (Examples III and IV) and provide relief from cytokine-mediated pain, swelling, fever and lethality as demonstrated using mouse, rat and rabbit model systems that are recognized in the art as predictors of efficacy in humans (Examples V to XII). Thus, the compounds described herein can be used as medicaments for the treatment of pathologies such as inflammation, pain, cachexia and patho-immunogenic diseases such as arthritis, inflammatory bowel disease and systemic lupus erythematosus, which are characterized by altered cytokine activity. In addition, the Examples provide evidence that a cytokine restraining agent of the present invention is useful in attenuating the negative aspects of disuse deconditioning (Example XIII), protecting organs, particularly after ischemia-reperfusion injury and cyclosporine-induced nephrotoxicity (Example XIV), reducing the nephrotoxic effects of cancer chemotherapy (Example XV), and treating disease states associated with nitric oxide, including diabetes and glomerulonephritis (Example XVI).

The following examples are intended to illustrate but not limit the present invention.

EXAMPLE I

Synthesis of Peptide Cytokine Restraining Agents

This example describes methods for the solid phase synthesis of peptide cytokine restraining agents.

A. Nle-Gln-His-(D)Phe-Arg-(D)Trp-Gly-$NH_2$

A peptide cytokine restraining agent having the amino acid sequence, Nle-Gln-His-(D)Phe-Arg-(D)Trp-Gly ("EX-1"), was synthesized using a modification of the solid phase peptide synthesis method of Merrifield (1964). Essentially, MBHA resin containing a t-BOC glycine derivative (Advanced Chemtech; Louisville, Ky.) was added to a reaction vessel suitable for solid phase peptide synthesis (see Houghten (1985), supra). The resin was washed three times with methylene chloride and the t-BOC protecting group was removed using trifluoroacetic acid (TFA) containing 1–2% anisole in methylene chloride. The resin then was washed with methylene chloride and treated with disopropylethylamine.

The peptide was extended by the addition of 3.2 equivalents of N-formyl-BOC-protected D-tryptophan in dimethylformamide and 3.0 equivalents of dicyclohexylcarbodiimide. The reaction was monitored using ninhydrin and was allowed to proceed for 25 min, after which the resin was washed using methylene chloride. The procedure was repeated using di-tolulyl-BOC arginine, then with each of the desired protected amino acids until the complete heptapeptide was synthesized.

Following synthesis of the heptapeptide, the N-formyl protecting group on the tryptophan residue was removed using 20% piperidine in DMF and the resin was washed with methylene chloride. The peptide was cleaved from the resin using anhydrous hydrogen fluoride (HF) containing 10% anisole, the reaction mixture was concentrated and the residue was extracted with aqueous acetic acid. The acetic acid fraction, which contained the dissolved sample, was removed and the residue was washed with water. The wash was added to the acetic acid fraction and the combined sample was concentrated. The resulting crude peptide was purified by RP-HPLC (Vydac, C-18 column, using a gradient of 1 to 60% solution B over 30 min (solution A is 0.1% TFA/water and solution B is 0.1% TFA/acetonitrile).

The peptide was determined to be 97% pure by RP-HPLC (Vydac C-18 column, using isocratic 24% solution B; solution A and solution B, as above; absorption determined at 215 nm). The mass of the purified heptapeptide was determined by plasma desorption mass spectrometry using a BioIon 20 Mass Analyzer time of flight detector. The mass of the EX-1 peptide was measured to be 942.7, which was essentially the same as the expected molecular mass (MS (M+1)=942.2).

B. His-(D)Phe-Arg-(D)Trp($CH_2$)-(NAc)Gly-$NH_2$

A cytokine restraining peptide of the invention, having the amino acid sequence His-(D)Phe-Arg-(D)Trp($CH_2$)-(NAc)Gly-$NH_2$, was synthesized and purified as described above, except for the following modifications. Boc-(D)Trp was converted to the corresponding N,O-dimethylhydroxamate using methyl chloroformate and N,O-dimethylhydroxyl amine hydrochloride. Reduction of the tryptophan amide with lithium aluminum hydride gave the Boc-(D)Trp aldehyde.

A solution of the Boc-(D)Trp aldehyde and sodium cyanoborohydride in DMF was added to glycine attached to the Rink amide resin in DMF containing 1% acetic acid. After the reductive amination was complete the secondary amine was acetylated with acetic anhydride and the resin was shaken with 1:1 trifluoroacetic acid and methylene chloride to remove the Boc group. Sequential coupling of the remaining amino acids was performed on an peptide synthesizer (Applied Biosystems) to produce the peptide His-(D)Phe-Arg-(D)Trp($CH_2$)-(NAc)Gly-$NH_2$. The peptide was cleaved from the resin and purified as described above.

EXAMPLE II

Preparation of Acetylated Peptide Cytokine Restraining Agents

This example describes methods for preparing N-acetylated peptide cytokine restraining agents.

The heptapeptide Nle-Gln-His-(D)Phe-Arg-(D)Trp-Gly was synthesized as described in Example I.A., except that prior to cleaving the newly synthesized peptide from the resin, the amino terminus of the peptide was acetylated by treating the sample with acetic anhydride, diisopropylethylamine and methylene chloride for 2 hr. Following acetylation, the heptapeptide was cleaved from the resin, purified by RP-HPLC and characterized by mass spectrometry, as described above. The acetylated heptapeptide of Example II, designated, here, as EX-2, was determined to be 98% pure and the mass was measured to be 985.2 daltons, which was same as the expected molecular mass.

Similar methods as described in Examples I and II were used to synthesize other cytokine restraining peptides of the invention, including Ac-(cyclohexyl)Gly-Gln-His-(D)Phe-Arg-(D)Trp-Gly-$NH_2$("EX-3"); Ac-(D)Phe-Arg-(D)Trp-$NH_2$ ("EX-4"); Ac-His-(D)Phe-Arg-(D)Trp-Gly-$NH_2$ ("EX-5"); and Ac-His-(D)Phe-Arg-(D)Trp-$NH_2$ ("EX-6"). Ac-His-(D)Phe-Arg-(D)Trp($CH_2$)-(NAc)Gly-$NH_2$ was prepared using the method described in Example I.B. except that, prior to cleaving the peptide from the resin, the peptide was acetylated using excess acetic anhydride.

EXAMPLE III

Reduction of Lipopolysaccharide-Induced Tumor Necrosis Factor Levels in Mice This example describes the effectiveness of two cytokine restraining agents for decreasing tumor necrosis factor (TNF) levels in lipopolysaccharide (LPS; endotoxin) treated mice.

Balb/c female mice weighing approximately 20 g were placed into two groups, a control group and a treated group. Five mg/kg of LPS in 0.9% saline was administered by intraperitoneal (IP) injection into the control mice. Mice in the treated group were first injected IP with 30 μg EX-2 or 150 μg EX-3 in saline, then, one mn after EX-2 or EX-3 was administered, the mice received LPS as described for the control group.

Blood samples were collected from the orbital sinus of treated and control mice at various times up to four hr after LPS was administered. The plasma was separated by centrifugation at 3000×g for 5 min, then diluted with four volumes of 1× phosphate buffer saline (pH 7.4) containing 1% bovine serum albumin. A 100 μl sample of serum was assayed by ELISA for TNF-α (Genzyme; Cambridge Mass.).

The mean (+/−SEM) TNF-α level in six mice from each group was determined and the percent reduction in TNF levels was calculated. As shown in Table I, treatment of mice with EX-2 resulted in a 50% decrease in the level of TNF-α as compared to untreated control mice. Similarly, treatment of mice with EX-3 resulted in a 56% decrease in the level of TNF-α as compared to untreated control mice and treatment with EX-4 resulted in a 53% decrease (Table II). These results indicate that the peptides of the invention can restrain LPS-induced cytokine activity.

EXAMPLE IV

Reduction of Lipopolysaccharide-Induced Interleukin-6 Levels in Mice

This example describes the effectiveness of a cytokine restraining agent for decreasing Interleukin-6 (IL-6) levels in LPS treated mice.

Balb/c mice were grouped and treated as described in Example III, above. Blood samples were obtained from the orbital sinus at various times up to six hr and serum was collected and diluted as described above. A 100 μl aliquot was assayed for IL-6 levels using an IL-6-specific ELISA by a modification of the method of Starnes et al., *J. Immunol.* 145:4185–4194 (1990), which is incorporated herein by reference.

The mean (+/−SEM) IL-6 level in six mice from each group was determined and the percent reduction in IL-6 was calculated. As shown in Table I, treatment of mice with EX-2 resulted in a 60% decrease in the level of IL-6 as compared to untreated control mice.

TABLE I

BIOLOGICAL DATA FOR CYTOKINE RESTRAINING AGENT, EX-2

| Biological Test | Dose | Efficacy |
|---|---|---|
| Reduction in TNF levels | 30 μg/mouse | 50% |
| Reduction in IL-6 levels | 300 μg/mouse | 60% |
| Reduction in Carageenan-induced Paw Swelling | 1 μg/mouse | 45% |
| Inhibition of LPS-induced Lethality | 11 × 300 μg/mouse | 83% |
| Reduction in IL-1-induced Hyperalgesia | 1 μg/mouse | 125% |
| Reduction in LPS-induced PMN Count | 100 μg/kg | 58% |
| Reduction in IL-1-induced Fever | 500 μg/kg | 52% |
| Reduction in LPS-induced Fever | 50 μg/kg<br>150 μg/kg | 45%<br>52% |
| Reduction in arachidonic acid-induced Ear Swelling | 100 μg/mouse | 72% |
| Reduction in Morphine-induced Respiratory Depression | 10 + 20 + 20 μg/kg/rabbit | 50% |

TABLE II

BIOLOGICAL DATA FOR CYTOKINE RESTRAINING AGENTS, EX-3 AND EX-4

| | | Efficacy | |
|---|---|---|---|
| Biological Test | Dose | EX-3 | EX-4 |
| Reduction in TNF levels | 150 μg/mouse | 56% | 53% |
| Reduction in Carageenan-induced Paw Swelling | 1 μg/mouse | 49% | NT |
| Inhibition of LPS-induced Lethality | 11 × 300 μg/mouse | 86% | 75% |
| Reduction in LPS-induced Fever | 150 μg/kg | 57% | 52% |
| Reduction in arachidonic acid-induced Ear Swelling | 100 μg/mouse | 62% | NT |
| Reduction in Morphine-induced Respiratory Depression | 10 + 20 + 20 μg/kg/rabbit | 65% | NT |

NT = not tested

EXAMPLE V

Carageenan-Induced Paw Swelling

This example describes the effectiveness of two cytokine restraining agents for alleviating inflammation and pain.

Carageenan-induced paw swelling was induced using a modification of the methods of Hiltz and Lipton, *Peptides* 11:979–982 (1990); Vinegar et al., *Fed. Proc.* 46:118–126 (1987); and Vinegar et al., *J. Pharmacol. Expt. Therap.* 166:96–103 (1969), each of which is incorporated herein by reference. Briefly, adult female Balb/c mice were anesthetized by IP injection of 7 mg/kg ketoamine and 0.6 mg/kg rompun. Foot pad thickness was measured using a spring loaded micrometer (Swiss Precision Instruments). Foot pad thickness was expressed in units of 1/100 inch. After baseline measurements were obtained, mice were injected into a hind foot pad with either 0.2 ml physiologic saline (control) or varying doses of EX-2 or EX-3 in 0.2 ml saline (treated). The first injection was followed immediately by injection of 0.02 ml of 0.15% κ-carageenan (Sigma Chemical Co.; St. Louis, Mo.).

Hind foot pad thickness was measured hourly for six hr, the change in thickness was determined and the percent reduction in swelling due to treatment with EX-2 was calculated. As shown in Tables I and II, IP injection of 1 μg EX-2 or 1 μg EX-3 reduced carageenan-induced swelling by 45% or 49%, respectively, when measured at the 2 hr time point.

EXAMPLE VI

Lipopolysaccharide-Induced Lethality

This example describes the effectiveness of the cytokine restraining agents, EX-2, and EX-3 and EX-4, in reducing lethality from sepsis induced by administration of LPS.

These experiments were performed based on information reported by Rivier et al., *Endocrinology* 125:2800–2805 (1989), which is incorporated herein by reference. Adult female Balb/c mice were provided food and water ad libitum. Mice were injected IP every four hr for 40 hr with 30 to 300 μg EX-2, EX-3 or EX-4 in 0.2 ml saline (treated group) or with 0.2 ml saline, alone (control group) (10 mice per group). Immediately following the first injection, 0.6 mg LPS endotoxin in 0.2 ml saline was administered to each mouse. Following LPS injection, EX-2 or saline was administered to the treated mice or the control mice, respectively, every 4 hr for 36 hr.

As shown in Tables I and II, administration of 3.3 mg EX-2, EX-3, or EX-4 (11 injections of 300 μg each) produced an 83%, 86%, and 75%, respectively, increase in survival as compared to control mice. These results demonstrate that intraperitoneal administration of the cytokine restraining peptides of the invention can reduce lethality due to LPS-induced sepsis.

EXAMPLE VII

Reduction in Interleukin-1β-Induced Hyperalgesia

This example describes the effectiveness of a cytokine restraining agent, EX-2, in providing pain prophylaxis.

These experiments were performed using a modification of the methods described by Poole et al., *Br. J. Pharmacol.* 106:489–492 (1992); Follenfant et al., *Br. J. Pharmacol.* 98:41–43 (1989) ; and Randall and Sellito, *Arch. Internatl. Pharmacodyn.* 111:409–419 (1957), each of which is incorporated herein by reference. Adult male Sprague-Dawley rats (175–275 g) were tested for hyperalgesia by a paw pressure technique using variable pressure instrumentation (IITC Life Sciences; Woodland Hills, Calif.). Rats were acclimated to the housing environment and were handled for three days prior to beginning a training session. On the day before the hyperalgesia experiments was to begin, each rat was placed into a sock and two variable paw pressure tests were performed 15 min apart.

The next day, the rats were pretested to determine the pressure (mm Hg) at which each animal exhibited escape reflexes such as whole body struggling and/or vocalization.

Approximately 5–10% of the rats were non-responders and were eliminated from further experiments.

Animals that responded to the paw pressure were pretreated by IP injection of various concentrations of EX-2 in a volume of 1 ml/kg (treated) or saline, alone (control). After 20 min, 100 μl of IL-1β (1U/100 μl) was administered to rats via intra plantar injection. Two hr after IL-1 administration, rats were subjected to two additional paw pressure tests and the increase in mm Hg of pressure that could be applied to the EX-2-treated rats as compared to the control rats was determined. As shown in Table I, treatment with 1 μg EX-2 increased the amount of pressure the rats would tolerate by 125% as compared to the control rats.

EXAMPLE VIII

Adult Respiratory Distress Syndrome

This example describes the effectiveness of a cytokine restraining agent, EX-2, in minimizing respiratory distress syndrome in LPS-treated rats.

These experiments were performed using a modification of the methods described by Ulich et al., *Am. J. Pathol.* 141:61–68 (1992) and by Wheelden et al., *Lab. Animals* 26:29–37 (1992), each of which is incorporated herein by reference. Male Harlan Sprague-Dawley rats were anesthetized using a mixture of 70 mg/kg ketamine and 6 mg/kg rompun injected IP. A 2–3 cm incision was made in the neck of each anesthetized rat and its trachea was exposed by blunt dissection of the surrounding soft tissue. The rats were suspended on a near vertical slab and intratracheal injections were performed by inserting into the exposed trachea, at a point 1 cm posterior to the larynx, a 25 G×½ inch needle attached to a 1 cc syringe.

Each rat received 0.5 ml/kg of saline or 0.5 ml/kg of 10 mg/ml (5 mg/kg) LPS endotoxin via slow intratracheal administration. Immediately following administration of the LPS endotoxin, rats were injected IP with 1 ml/kg of either saline (control) or saline containing various concentrations of EX-2 (treated). The rats were maintained in the elevated position for 1–2 min to facilitate distribution of the LPS and saline into the lung. The incisions were closed and the rats were allowed to recover. Two and four hr post-intratracheal injection, saline or EX-2 again was administered IP to control and treated rats, respectively.

At 6 hr post-intratracheal injection, the rats were re-anesthetized and exsanguinated via cardiac puncture. Serum was collected and saved. The neck and chest were opened to expose the trachea and lungs, the lungs were lavaged with 6×5 ml saline using a 27 G×¾ inch needle and the lavage fluid was pooled.

The total polymorphonuclear leukocytes (PMN;

neutrophils) in the broncho-alveolar lavage fluid were counted in the EX-2-treated rats and compared with the number in the control rats. As shown in Table I, treatment with 100 μg/kg EX-2 inhibited the increase in PMN infiltration in LPS-treated lungs by 58%.

EXAMPLE IX

Inhibition of Interleukin-1β- or Lipopolysaccharide-Induced Temperature Increase This example describes the effectiveness of the cytokine restraining agents, EX-2, EX-3 and EX-4, at inhibiting body temperature increase in rats in response to two different agents.

Male Wistar rats (45–75 days old) were placed in a temperature controlled room held at 26° C., which is thermoneutral for the normal body temperature of rats, and were maintained in the room with free access to food and water for 24 hr prior to testing. On the morning of the study, rats were marked for identification and weighed. The temperature of each rat was determined by placing the animal in a restraining cage designed to minimize stress and inserting a temperature probe (YSI probe #402) 3–5 cm into the animal's rectum. The temperature was recorded 15 sec after the reading stabilized. Measurements were repeated 1 hr later to establish a baseline temperature for each rat.

After the baseline temperatures were established, rats were injected IP with saline, IL-1β or LPS endotoxin.

Rats then were injected IP with either saline (control) or various concentrations of EX-2, EX-3, or EX-4 (treated). The temperature of the rats was measured every hr for 6 hr and the inhibition by EX-2, EX-3, or EX-4 of the rise in temperature due to IL-1β or LPS was determined.

As shown in Table I, treatment with 500 μg/kg EX-2 inhibited IL-1-induced fever by 52%. In addition, treatment with 50 or 150 μg/kg EX-2 inhibited LPS-induced fever by 45% or 52%, respectively, when measured 6 hr following LPS injection. Furthermore, treatment with 150 μg/kg EX-3 or EX-4 inhibited LPS-induced fever by 57% and 52%, respectively (Table II). These results demonstrate that various cytokine restraining peptides of the invention can effectively reduce fever.

EXAMPLE X

Reduction of Arachidonic Acid-Induced Ear Swelling in Mice

This example demonstrates that EX-2 and EX-3 can reduce arachidonic acid-induced ear swelling in mice.

Experiments were performed using female Balb/c mice weighing 18–23 grams. Saline or 100 μg EX-2 or EX-3 was administered IP, 30 min prior to topical application of arachidonic acid (AA). A 10 μl pipet was used to apply 10 μl AA solution (100 mg/ml ethanol; Calbiochem-Novabiochem; San Diego Calif.) to the inner and outer surfaces of the right ear of each mouse. Ten μl ethanol, alone, was applied to the inner and outer surface of the left ear of each mouse.

Ear thickness was measured with a hand-held spring loaded caliper immediately before and 60 min after AA application. Increase in ear thickness was calculated by subtracting the change observed in the control ear from the change observed in AA-treated ear. The value for each group (saline and control) is the average of the swelling observed in the individual mice in each group. The percent reduction of swelling is based on the swelling observed in the saline control group. As shown in Tables I and II, EX-2 and EX-3 reduced AA-induced ear swelling by 72% and 62%, respectively.

EXAMPLE XI

Reduction of Morphine-Induced Respiration Depression in Rabbits

This example demonstrates that EX-2 and EX-3 can reduce the depression in respiration induced by morphine in rabbits.

Male Shelton rabbits (3–4 kg) were restrained and fitted around the thorax, just behind the front limbs, with a respiration transducer (Model F-RCT; Grass Instruments; Quincy Mass.). The transducer was connected to a grass polygraph via an EKG cable. An intravenous line was established for drug administration by cannulating the marginal ear vein using a 25 G butterfly needle.

Rabbit breathing was allowed to stabilize, then morphine sulfate (2 mg/kg in 0.5 ml saline) was administered by intravenous (iv) injection and respiratory rate and depth were monitored for 10 min. A second dose of morphine was administered, then, after 10 min, EX-2 or EX-3 (10 μg/kg in 0.5 ml saline) was administered, iv, and rabbits were monitored for 20 min. Two additional doses of EX-2 or EX-3 (20 μg/kg in 1.0 ml saline) were administered at 20 min intervals, i.e., 40 min and 60 min after the first morphine injection.

Results were calculated as the percent change from baseline values and are expressed as the difference of the mean value of the treated group minus the mean value of the control group at the end of the experiment (80 min). As shown in Tables I and II, EX-2 and EX-3 reduced the morphine-induced respiratory depression in rabbits by 50% and 65%, respectively.

EXAMPLE XII

Effect of Orally Administered Cytokine Restraining Agents in Reducing TNF-α Levels and LPS-induced Lethality This example describes the oral effectiveness of various cytokine restraining agents in reducing LPS-induced TNF-α levels and lethality in mice.

The LPS-induced lethality studies were performed based on information reported by Rivier et al., supra, 1989. Adult female Balb/c mice were provided food and water ad libitum. Mice were administered 150 μg or 300 μg EX-2, EX-3, EX-5 or EX-6 in 100 μl saline by gavage every 4 hr for 40 hr (total doses of 1.65 mg and 3.3 mg, respectively). Control mice received 100 μl saline, alone. Immediately following the first dose of cytokine restraining agent or saline, 0.6 mg LPS in 0.2 ml saline was administered by IP injection. A statistically significant increase in survival was observed in mice receiving 3.3 mg EX-5 (63%), 1.65 mg EX-6 (68%) or 3.3 mg EX-5 (44%) as compared to control mice (0%) or mice receiving EX-2 or EX-3 (0% to 11%).

The ability of orally administered cytokine restraining agents to reduce LPS-induced TNF-α levels also was examined. Balb/c female mice (20 g) were administered 150 μg or 300 μg EX-2, EX-3, EX-5 or EX-6 in 100 μl saline by gavage. Control mice received 100 μl saline, alone. One mn later, 0.1 mg LPS was administered by IP injection. Samples were collected and TNF-α levels were determined as described in Example III, above.

The mean TNF-α levels in the mice from each group (n=9–20) was determined and the percent reduction in TNF-α levels was calculated. TNF-α levels were significantly reduced in mice receiving 150 μg EX-3 (49%); 300 μg EX-3 (40%) or 300 μg EX-5 (44%) as compared to control mice (0%) and mice receiving EX-2 (26% to 28%). These results demonstrate that various cytokine restraining agents of the invention are effective when administered orally.

EXAMPLE XIII

Disuse Deconditioning in Rats

This experiment describes the effectiveness of a cytokine restraining agent, EX-2, in ameliorating the negative effects associated with 14 days disuse deconditioning in rats.

Adult male Sprague-Dawley rats (355–365 g) were used in this study. Animals were housed individually in standard rat cages and were acclimated on a treadmill for 4 days. The next day, a baseline tail bleed was performed, followed by a maximal treadmill stress test the day after. The day following the stress test, the animals were divided into the appropriate treatment and control groups and the animals were suspended by their tails in suspension cages, which simulates weightlessness and, therefore, deconditions the animals. Another group of control animals was placed in standard rat cages with grated flooring similar to that utilized in the suspension cages. All animals were housed one per cage and supplied with food and water ad libitum. Body weights and food consumptions were measured daily. Animals received twice daily IP injections of 1 μg/kg or 5 μg/kg body weight of EX-2 (treated), or 1 ml/kg body weight of saline (control). On day 10, all animals were stress tested on the treadmill until they reached exhaustion. Data on maximum $VO_2$ and running time were collected and compared to pre-suspension results. On day 14, all animals were sacrificed, and blood, tissues, and organs were collected for further analysis. All procedures and tests were performed blind to avoid researcher subjectivity. Statistical significance ($p<0.05$) between groups was evaluated by ANOVA with Student-Newman-Keuls test for multiple comparisons. All data are reported as the mean ± standard error (SE).

Body weights decreased significantly for all suspended animals, regardless of treatment. Food consumption was not significantly different between the groups. All of the animals were subjected to the stress tests, which measured exercise time and maximal $VO_2$. As well, levels of the oxidative enzyme soleus citrate synthase and tibia bone density were measured.

As summarized in Table III, EX-2 exhibits a significant effect on many of the parameters associated with disuse deconditioning. Twice daily injections of low doses of EX-2 (1 or 5 μg/kg) significantly attenuated the deconditioning effects on exercise time, maximal $VO_2$, soleus citrate synthase levels, and tibia bone density. More specifically, EX-2 significantly attenuated both exercise performance parameters, exercise time and maximal $VO_2$, 44% and 80%, respectively, when compared to the decrease between the saline control and suspended animals. Soleus citrate synthase was attenuated by 50%. Tibia bone density measurements showed that EX-2 significantly attenuated suspension-induced bone demineralization by 50%. These results demonstrate that administration of a cytokine restraining peptide of the present invention reduces the negative effects of disuse deconditioning.

TABLE III

DISUSE DECONDITIONING

| Variable | % Attenuation* |
|---|---|
| Exercise Time | 44%** |
| Maximal $VO_2$ | 80%** |
| Soleus Citrate Synthase | 50%** |
| Tibia Bone Density | 50%** |

*% Attenuation of suspension-induced decrease of suspended groups as compared to control group.
**Significantly ($p < 0.05$) greater than suspended controls.

EXAMPLE XIV

Organ Protection

This example describes the effectiveness of a cytokine restraining agent, EX-2, in preventing kidney damage in two rat models, an ischemia-reperfusion model and a cyclosporine-induced nephrotoxicity model.

A. Ischemia-Reperfusion Injury: These experiments were performed to determine if a peptide which has cytokine restraining properties, EX-2, can ameliorate the reperfusion-induced vasoconstriction and reduction in glomerular filtration rate that results from clamping of the renal artery. As a comparison, the NSAID ketorolac was utilized in the same model.

Sprague-Dawley rats (250–300 g) were anesthetized with Inactin® (120 mg/kg). After deep anesthesia was assured, the rats were cannulated in the trachea with polyethylene (PE) tubing (PE 240), jugular vein, femoral artery, bladder (PE 50 for previous 3 cannulations), and left ureter (stretched PE 50). Once cannulation was completed, a 2 cm flank incision above the left kidney was performed and the renal pelvis and vascular bundle were exposed. The tissue surrounding the left renal artery was gently dissected away from the artery. The exposed renal artery was clamped for 1 hr using a small vascular cross-over clamp.

Just prior to clamping, EX-2 (50 or 500 μg/kg), ketorolac (KETO, 1 mg/kg), or vehicle was administered intravenously (iv) After 1 hr of clamping (ischemia), the clamp was gently removed with care taken to avoid damaging either the renal artery or nerves. An infusion of $^3$H-Inulin (NEN/Dupont; Wilmington, Del.), (0.6 μCi/ml in phosphate buffered saline (PBS)) (2 ml/hr) was initiated at a constant rate of 4 μCi/hr. After 60 min of reperfusion, glomerular filtration rate (GFR), renal plasma flow (RPF) and renal vascular resistance (RVR) were assessed in two 30 min collection periods. The kidney was then removed for analysis. Sham operated and clamped rats served as controls for the above group. Contralateral renal function was utilized to determine the stability of the rat's renal function during the measured period. The results demonstrate that EX-2 effects an increase in glomerular filtration rate and decrease in vascular resistance (Table IV). This data provides that a present cytokine restraining agent effectively protects the kidney against damage associated with ischemia-reperfusion.

TABLE IV

RENAL ISCHEMIA/RESPERFUSION (I/R)

| | GFR | RVR (ml/mm) | RPF |
|---|---|---|---|
| Sham | 1.0 ± 0.1 | 1.0 ± 0.1 | 4.2 ± 0.4 |
| I/R + PBS | 0.2 ± 0.1 | 6.6 ± 2.1 | 0.8 ± 0.2 |
| I/R + EX-2 | 0.5 ± 0.1 | 1.8 ± 0.2 | 2.3 ± 0.3 |

B. Cyclosporine-Induced Nephrotoxicity: This experiment as performed to ascertain if EX-2 can mitigate the reduction in glomerular filtration rate (GFR) and renal blood flow, as well as the dysfunction in fluid and electrolyte homeostasis induced by immunosuppressive treatment with cyclosporine A.

In the first study, male Sprague-Dawley rats (n=43) with a weight range of 240–290 g at the initiation of the cyclosporine A (CsA) treatment were divided into 4 weight matched groups. The groups were as follows: (1) Control: no CsA, no EX-2, treatment only with CsA vehicle (PBS) PO and EX-2 vehicle (also PBS) IP; (2) CsA: treatment with CsA (50 mg/kg in PBS administered PO daily at 0830 hr for 9 days) and IP injections of PBS (Ex-2 vehicle); (3) CsA and 50 μg: CsA treatment identical to group 2 with the addition of EX-2 (50 μg/kg IP administered daily at 0800 and 1700 hr in EX-2 vehicle); and (4) CsA and 500 μg: CsA treatment identical to groups 2 and 3, and EX-2 treatment protocol similar to group 3 except that the dose of EX-2 was 500 μg/kg BW. After deep anesthesia was assured, the rats were cannulated in the trachea (PE 240) jugular vein, femoral artery, and bladder (PE 50 for the previous 3 cannulations). After cannulation, infusion of $^3$H-inulin was initiated 50 min prior to the measurement period to assess glomerular filtration rate, renal blood flow and plasma flow. Renal blood flow was determined by the inulin extraction technique. At the end of the study, the kidneys were removed for histological analysis.

In the second study, male Sprague-Dawley rats (n=31) with a weight range of 240–290 g at the time of initiation of the cyclosporine treatment were divided into 4 weight-matched groups. The time course and protocol of this study matched the first study with the following exceptions: (1) The daily dose of CsA was reduced to 30 mg/kg and was administered subcutaneously (SC) and (2) the 50 μ/kg dose of EX-2 was substituted with a twice daily dose of 200 μg/kg. The 500 μg/kg dose of EX-2 was repeated in this study. Renal hemodynamics were determined and extracellular fluid volumes were also assessed.

CsA treatment did not significantly decrease renal blood flow in these studies due to the scatter in the data. However, EX-2 treatment improved blood flow to values not different from control. In the second study, where extracellular fluid volumes (ECF) were measured, there were no differences in ECF among control and treatment groups (27.6±1.9 in control, 27.5±1.7 in CsA and vehicle, 26.2±0.9 in CsA+200 μg/kg EX-2, and 25.7±1.4% in CsA+500 μg/kg EX-2).

Figure 1B:
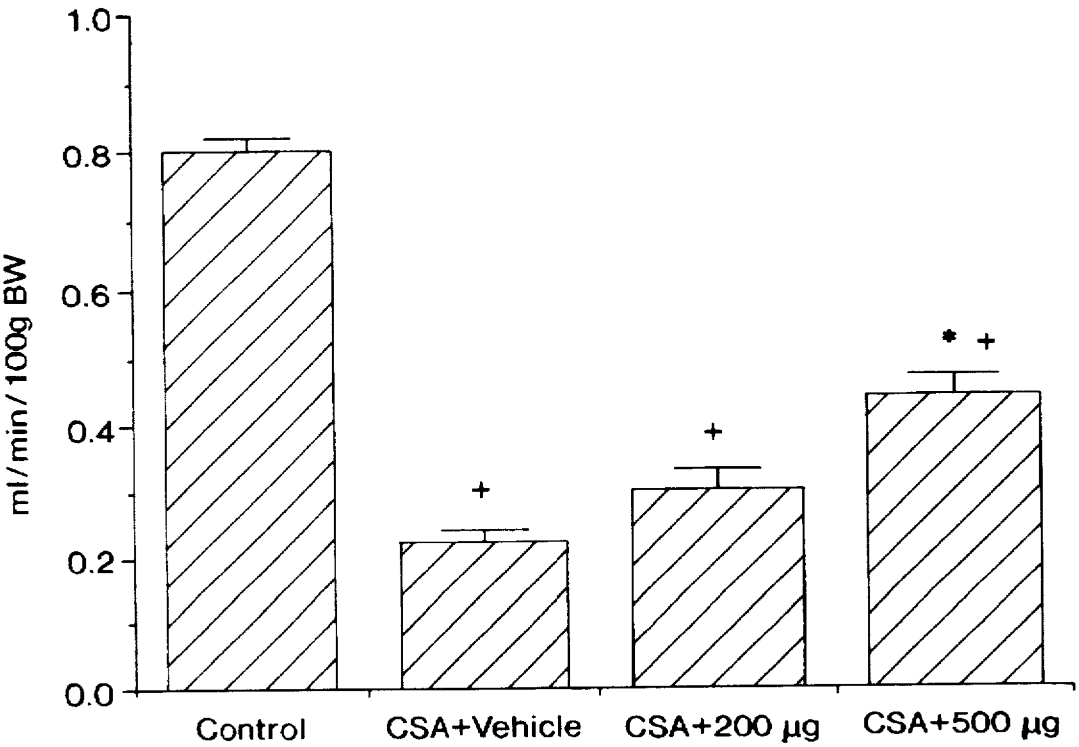

Urinary protein excretion was also measured and the data demonstrated that EX-2 treatment did not increase urinary protein excretion compared to CsA-treated rats despite the significant increase in GFR. EX-2 significantly increased GFR, compared to CsA and vehicle controls, in both studies and returned renal blood flow to values not different from control. There were no changes in ECF as a result of EX-2 treatment and there was a trend to decreased urinary protein excretion normalized to glomerular filtration rate. The results from the two experiments are shown in FIGS. 1*a* and 1*b* and provide evidence that a cytokine restraining peptide of the present invention reduces cyclosporine-induced nephrotoxicity and the damage caused thereby.

EXAMPLE XV

Cancer Chemotherapy

This example describes the effectiveness of a cytokine restraining agent, EX-2, in reducing the nephrotoxic effects of cancer chemotherapeutic agents.

Male Sprague-Dawley were used to determine the effect of EX-2 on renal function after cisplatin (CDDP) administration. All rats were administered CDDP (4 mg/kg IP) and divided in 3 treatment groups (n=6/group). The groups were as follows: (1) Administration with vehicle and sterile PBS 3×/day; (2) Administration of EX-2 at a dose of 5 μg/kg 3×/day; and (3) same as group 2 except the dose of EX-2 was 50 μg/kg 3×/day.

An infusion of $^{3}$H-inulin (0.6 μCi/ml in PBS) (2 ml/hr) was initiated at the end of the surgical preparation period. The continuous infusion was started 60 min prior to the renal function measurements and maintained to the end of the study. Glomerular filtration was assessed by inulin clearance techniques in two 30 min periods and renal blood flow (RBF) and renal plasma flow (RPF) were measured by inulin extraction techniques (arterial vs. renal vein inulin concentration) from left kidney renal vein blood sampled at the end of the second GFR measurement period. Urinary output was also monitored to determine both urine flow and fractional excretion of water. Urinary electrolyte ($Na^+$ and $K^+$) concentrations were analyzed by flame photometry (Model 51 Ca, Bacharch, Inc.; Pittsburgh, Pa.) and urinary protein concentrations were determined. At the end of the measurement periods, the kidneys were removed for histological analysis. The influence of varying treatment doses of EX-2 on renal function in 3 CDDP administered rats (CDDP at 4 mg/kg IP) is summarized in Table V. The data demonstrates that a cytokine restraining peptide of the present invention increases glomerular filtration rate, renal plasma flow and renal blood flow, thereby reducing the nephrotoxicity of a cancer chemotherapeutic agent.

TABLE V

CANCER CHEMOTHERAPY

| | GFR | RPF (ml/mm) | RBF |
|---|---|---|---|
| CDDP + vehicle | 1.0 ± 0.4 | 5.6 ± 0.9 | 10.2 ± 1.6 |
| CDDP + 5 μg/kg | 0.8 ± 0.2 | 6.5 ± 1.0 | 12.1 ± 2.0 |
| CDDP + 50 μg/kg | 1.6 ± 0.4 | 8.8 ± 1.1 | 16.8 ± 2.2 |

Example XVI

Treatment of Diseases Mediated by Nitric Oxide and Cytokines

This example describes the effectiveness of EX-2 at inhibiting inducible nitric oxide synthase (INOS) and decreasing glucose in streptozotozin-induced diabetes and in reducing albumin levels in glomerulonephritis.

A. Inducible Nitric Oxide Synthase (INOS): Rat aorta smooth muscle cells (RASMC) were isolated from male rats (325–350 g) using the previously published procedures of Gelsterfer et al., *Circ. Res.* 62:749–756 (1988), which is incorporated herein by reference. Cells were positively identified as smooth muscle cells by indirect immunofluorescent staining for anti-α-actin, using a mouse anti-α-actin antibody and anti-mouse IgG FITC conjugate. Cells were grown in T-75 tissue culture flasks (Corning Delbelco's Glass, Inc.; Corning, N.Y.) in 50% F12 and 50% Delbelco's Modified Eagle Medium (DMEM) supplemented with 10% bovine serum, 0.2 g/l L-glutamine, penicillin (100 U/ml) and streptomycin (0.1 mg/ml).

Cells between passages 1–5 were pretreated with one of the following: vehicle, LPS (1 μg/ml), IL-1β (10 U/ml), or TNF-α (100 U/ml) for 6 hr. In similar groups, 0.1 or 1 μM of EX-2 was added 10 min before the addition of LPS, IL-1β or TNF-α. Six hr later, cells were washed with Earle's balanced salt solution and incubated for 30 min with vehicle of 100 μM L-nitro arginine methyl ester (L-NAME). Accumulation of cGMP was determined following exposure to 0.3 mM 3-isobutyl-1-methyl xanthine (IBMX) in the presence or absence of 1 mM L-arginine. Medium was then rapidly aspirated and 500 μl of 0.1N HCl was added to each well to stop the reactions and extract cGMP. Thirty min later, the HCl extract was collected and cell remnants removed from the wells by adding hot 1.0N NaOH and scraping the well with a rubber policeman. The HCl extract was analyzed for cGMP by RIA and the NaOH-solubilized cell remnants were used for protein determination.

Male Sprague-Dawley rats were anesthetized with 55 mg/kg pentobarbital IP. Catheters were inserted into the carotid artery and jugular vein for blood withdrawal and drug administration, respectively. EX-2 or saline was given to a group of 6 rats. One hr later, while rats were still under anesthesia, blood was withdrawn into a heparinized syringe and plasma was obtained by centrifugation. RASMC were incubated with plasma from control or EX-2-treated animals and the ability of plasma components to inhibit the induction of INOS by LPS or IL-1β was determined as above.

The radioligand ($^{125}$I-succinyl cGMP-tyrosine methyl ester) was prepared by the method of Hunter and Greenwood *Nature,* 94:495–496 (1962), which is incorporated herein by reference, using carrier free $^{125}$I. The iodination reaction products were separated by RP-HPLC following the procedures of Patel and Lindent, *Anal. Biochem.* 168:417–425 (1988), which is incorporated herein by reference. Using a monoclonal antibody for cGMP, RIA was performed in the Gammaflow™ automated RIA system as disclosed in Brooker et al., *Science* 191:270–276 (1976), which is incorporated herein by reference. Standard stock solutions of cGMP (20 μM) were prepared in 0.1N HCl and the absorbance of the solution was routinely monitored spectrophotometrically (Shimadzu, UV 160U). Standard dilutions (0.63–80 nM) were made from stock solution. The HCl extract containing cGMP was used for RIA directly. Results are summarized in Table V below and demonstrate that EX-2 can inhibit inducible nitric oxide synthase, thereby reducing levels of NO production and the negative effects associated therewith, such as diabetes or glomerulonephritis.

B. Induced Diabetes: Male Sprague-Dawley rats were given 65 mg/kg of streptozotocin (STZ) intravenously through the tail vein. Rats were divided into two groups. The first group was administered EX-2, 150 μg/kg every 8 hr for 72 hr and the second group was a control. Blood samples were withdrawn under ether anesthesia every 8 hr for the first 72 hr, then every 12 hr or 24 hr until the end of the observation period. Plasma samples were assayed for glucose using a glucose assay kit (Trinder, Sigma Chemical Co.). As shown in Table VI below EX-2 effect a 72% reduction in blood glucose levels.

C. Glomerulonephritis: Male Sprague-Dawley rats (weight 194–248 g) were immunized by subcutaneous injection of 1 mg normal rabbit IgG (Sigma Chemical Co.) in Freund's complete adjuvant (Sigma Chemical Co.). EX-2 was administered 3 times per day (100 μg/kg per injection) throughout the duration of the experiment. Seven days later, the rats were injected with 1.5 ml of nephrotoxic serum iv via dorsal penile vein. Urine, plasma, and serum were collected before injection of nephrotoxic serum at 4, 6, 24, 48, and 96 hr thereafter. All rats developed acute glomerulonephritis with albuminuria that increased progressively from 4 to 96 hr, as demonstrated by 24 hr albumin excretion. Albuminuria was quantified by immunoelectrophoresis. The results are summarized below in Table VI and show that a cytokine restraining agent of the present invention attenuates the increase in albumin levels seen in glomerulonephritis, which is an indication of improvement in the disease state.

In summary, the above data demonstrate that a cytokine restraining peptide of the present invention inhibits inducible nitric oxide synthase levels, thereby reducing the production of NO. The cytokine restraining agents are also useful for treating particular diseases associated with nitric oxide, such as diabetes and glomerulonephritis.

TABLE VI

DIABETES AND GLOMERULONEPHRITES

| Model/Assay | Measure | % Reduction* |
|---|---|---|
| INOS | cGMP (pmol/100 mg/5 min) | 60% |
| STZ Diabetes | Blood Glucose (mg/dl) | 72% |
| Glomerulonephritis | Albumin (mg/day) | 62% |

*Percent reduction of increases in measures that were induced by Model/Assay by administration of EX-2.

Although the invention has been described with reference to the examples provided above, it should be understood that various modifications can be made by those skilled in the art without departing from the invention. Accordingly, the invention is set out in the following claims.

We claim:

1. A method of reducing the effects of disuse deconditioning in a subject, comprising administering to the subject an effective amount of a cytokine restraining peptide, comprising:

$X_1$-$X_2$-His-(D)Phe-Arg-(D)Trp-$X_3$, wherein:

$X_1$ is

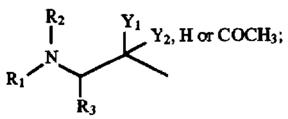

$X_2$ is

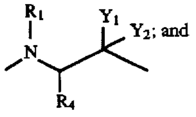

$X_3$ is

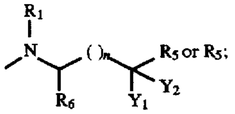

wherein $Y_1$ and $Y_2$ are independently a hydrogen atom, or are taken together to form a carbonyl or thiocarbonyl;

$R_1$ is H, $COCH_3$, $C_2H_5$, $CH_2Ph$, COPh, $COOCH_2Ph$, COO-t-butyl, $CH_2CO$-(polyethylene glycol) or A;

$R_2$ is H or $COCH_3$;

$R_3$ is a linear or branched alkyl group having 1 to 6 carbon atoms or a cyclic alkyl group having 3 to 6 carbon atoms;

$R_4$ is $(CH_2)_m$—$CONH_2$, $(CH_2)_m$—$CONHR_1$ or $(CH_2)_m$—CONHA;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

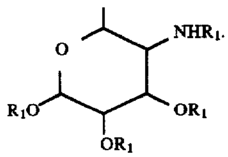

2. A method of protecting an organ of a subject against organ damage, comprising administering to the subject an effective amount of a cytokine restraining peptide, comprising:

$X_1$-$X_2$-His-(D)Phe-Arg-(D)Trp-$X_3$, wherein:

$X_1$ is

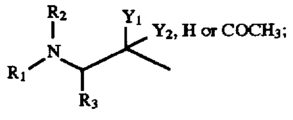

$X_2$ is

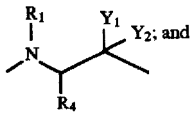

$X_3$ is

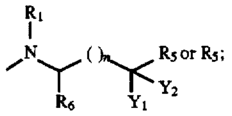

wherein $Y_1$ and $Y_2$ are independently a hydrogen atom, or are taken together to form a carbonyl or thiocarbonyl;

$R_1$ is H, $COCH_3$, $C_2H_5$, $CH_2Ph$, COPh, $COOCH_2Ph$, COO-t-butyl, $CH_2CO$-(polyethylene glycol) or A;

$R_2$ is H or $COCH_3$;

$R_3$ is a linear or branched alkyl aroup having 1 to 6 carbon atoms or a cyclic alkyl group having 3 to 6 carbon atoms;

$R_4$ is $(CH_2)_m$—$CONH_2$, $(CH_2)_m$—$CONHR_1$ or $(CH_2)_m$—CONHA;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

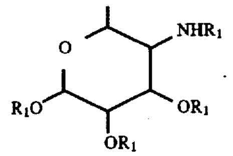

3. The method of claim 2, wherein the organ damage is the result of a condition selected from the group consisting of organ transplant, the administration of an immunosuppressive agent, and ischemia-reperfusion.

4. The method of claim 3, wherein the immunosuppressive agent is cyclosporine.

5. A method of reducing a negative effect of cancer chemotherapy in a subject, comprising administering to the subject an effective amount of a cytokine restraining peptide, comprising:

$X_1$-$X_2$-His-(D)Phe-Arg-(D)Trp-$X_3$, wherein:

$X_1$ is

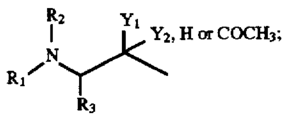

$X_2$ is

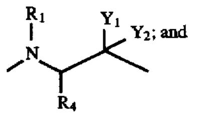

$X_3$ is

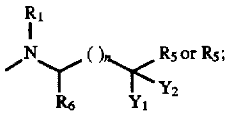

wherein $Y_1$ and $Y_2$ are independently a hydrogen atom, or are taken together to form a carbonyl or thiocarbonyl;

$R_1$ is H, $COCH_3$, $C_2H_5$, $CH_2Ph$, COPh, $COOCH_2Ph$, COO-t-butyl, $CH_2CO$-(polyethylene glycol) or A;

$R_2$ is H or $COCH_3$;

$R_3$ is a linear or branched alkyl group having 1 to 6 carbon atoms or a cyclic alkyl group having 3 to 6 carbon atoms;

$R_4$ is $(CH_2)_m$—$CONH_2$, $(CH_2)_m$—$CONHR_1$, or $(CH_2)_m$—CONHA;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the aeneral formula:

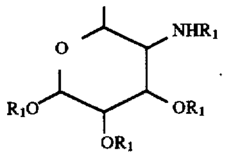

6. A method of claim 5, wherein the negative effect is the nephrotoxic effect of a cancer chemotherapeutic agent.

7. The method of claim 6, wherein the cancer chemotherapeutic agent is selected from the group consisting of cisplatin, Taxol®, and Adriamycin®.

8. A method of reducing the effects of disuse deconditioning in a subject, comprising administering to the subject an effective amount of a cytokine restraining peptide, comprising:

$X_4$-$X_5$-(D)Phe-Arg-(D)Trp-$X_3$, wherein:

$X_4$ is

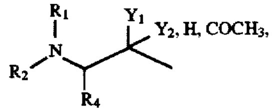

$X_5$ is His, H, or $COCH_3$; and $X_3$ is

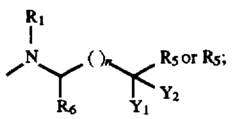

wherein $Y_1$ and $Y_2$ are independently a hydrogen atom, or are taken together to form a carbonyl or thiocarbonyl;

$R_1$ is H, $COCH_3$, $C_2H_5$, $CH_2Ph$, COPh, $COOCH_2Ph$, COO-t-butyl, $CH_2CO$-(polyethylene glycol) or A;

$R_2$ is H or $COCH_3$;

$R_3$ is a linear or branched alkyl group having 1 to 6 carbon atoms or a cyclic alkyl group having 3 to 6 carbon atoms:

$R_4$ is $(CH_2)_m$—$CONH_2$, $(CH_2)_m$—$CONHR_1$ or $(CH_2)_m$—CONHA;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

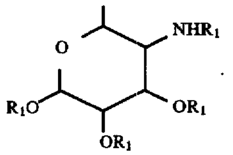

9. A method of protecting an organ of a subject against organ damage, comprising administering to the subject an effective amount of a cytokine restraining peptide, comprising:

$X_4$-$X_5$-(D)Phe-Arg-(D)Trp-$X_3$, wherein:

$X_4$ is

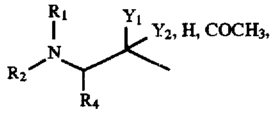

or absent;

$X_5$ is His, H, or $COCH_3$; and $X_3$ is

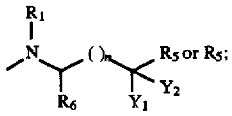

wherein $Y_1$ and $Y_2$ are independently a hydrogen atom, or are taken together to form a carbonyl or thiocarbonyl;

$R_1$ is H, $COCH_3$, $C_2H_5$, $CH_2Ph$, COPh, $COOCH_2Ph$, COO-t-butyl, $CH_2CO$-(polyethylene glycol) or A;

$R_2$ is H or $COCH_3$;

$R_3$ is a linear or branched alkyl group having 1 to 6 carbon atoms or a cyclic alkyl group having 3 to 6 carbon atoms;

$R_4$ is $(CH_2)_m$—$CONH_2$, $(CH_2)_m$—$CONHR_1$ or $(CH_2)_m$—CONHA;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

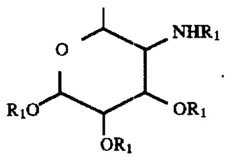

10. The method of claim 9, wherein the organ damage is the result of a condition selected from the group consisting of organ transplant, the administration of an immunosuppressive agent, and ischemia-reperfusion.

11. The method of claim 10, wherein the immunosuppressive agent is cyclosporine.

12. A method of reducing a negative effect of cancer chemotherapy in a subject, comprising administering to the subject an effective amount of a cytokine restraining peptide, comprising:

$X_4$-$X_5$-(D)Phe-Arg-(D)Trp-$X_3$, wherein:

$X_4$ is

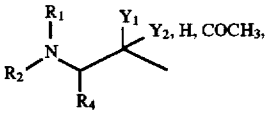

or absent;

$X_5$ is His, H, or $COCH_3$; and $X_3$ is

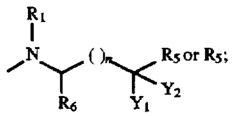

wherein $Y_1$ and $Y_2$ are independently a hydrogen atom, or are taken together to form a carbonyl or thiocarbonyl;

$R_1$ is H, $COCH_3$, $C_2H_5$, $CH_2Ph$, COPh, $COOCH_2Ph$, COO-t-butyl, $CH_2CO$-(polyethylene glycol) or A;

$R_2$ is H or $COCH_3$;

$R_3$ is a linear or branched alkyl group having 1 to 6 carbon atoms or a cyclic alkyl group having 3 to 6 carbon atoms:

$R_4$ is $(CH_2)_m$—$CONH_2$, $(CH_2)_m$—$CONHR_1$ or $(CH_2)_m$—CONHA;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

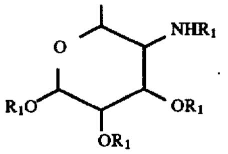

13. A method of claim 12, wherein the negative effect is the nephrotoxic effect of a cancer chemotherapeutic agent.

14. The method of claim 13, wherein the cancer chemotherapeutic agent is selected from the group consisting of cisplatin, Taxol®, and Adriamycin®.

15. The method of claim 1, 2, 5, 8, 9 or 12 wherein the amino terminus of the cytokine restraining peptide is modified.

16. The method of claim 15, wherein the amino terminus of the cytokine restraining peptide is acetylated.

17. The method of claim 1, 2, 5, 8, 9 or 12, wherein the carboxyl terminus of the cytokine restraining peptide is modified.

18. The method of claim 17, wherein the carboxyl terminus of the cytokine restraining peptide is amidated.

19. The method of claim 1, 2, 5, 8, 9 or 12 wherein $R_1$ is selected from the group consisting of H, $C_2H_5$ and $CH_2Ph$.

20. The method of claim 19, wherein $R_1$ and $R_2$ each are H.

21. A method of reducing the effects of disuse deconditioning in a subject, comprising administering to the subject an effective amount of the cytokine restraining peptide Ac-Nle-Gln-His-(D)Phe-Arg-(D)Trp-Gly-$NH_2$.

22. A method of protecting an organ of a subject against organ damage, comprising administering to the subject an effective amount of the cytokine restraining peptide Ac-Nle-Gln-His-(D)Phe-Arg-(D)Trp-Gly-$NH_2$.

23. A method of reducing a negative effect of cancer chemotherapy in a subject, comprising administering to said subject an effective amount of a cytokine restraining peptide Ac-Nle-Gln-His-(D)Phe-Arg-(D)Trp-Gly-$NH_2$.

24. A cytokine restraining peptide selected from the group consisting of:

(D)Phe-Arg-(D)Trp;

Ac-(D)Phe-Arg-(D)Trp;

(D)Phe-Arg-(D)Trp-$NH_2$; and

Ac-(D)Phe-Arg-(D)Trp-$NH_2$.

25. A method of restraining pathologically elevated cytokine activity in a subject, comprising administering to the subject an effective amount of the cytokine restraining peptide of claim 24.

26. A composition of matter, comprising a pharmaceutically acceptable carrier and a cytokine restraining peptide selected from the group consisting of:

(D)Phe-Arg-(D)Trp;

Ac-(D)Phe-Arg-(D)Trp;

(D)Phe-Arg-(D)Trp-$NH_2$; and

Ac-(D)Phe-Arg-(D)Trp-$NH_2$.

27. A cytokine restraining peptide, having the sequence of (D)Phe-Arg-(D)Trp-$X_3$, wherein $X_3$ is

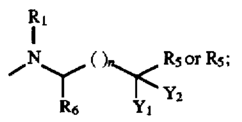

wherein $Y_1$ and $Y_2$ are independently a hydrogen atom, or are taken together to form a carbonyl or thiocarbonyl;

$R_1$ is H, $COCH_3$, $C_2H_5$, $CH_2Ph$, COPh, $COOCH_2Ph$, COO-t-butyl, $CH_2CO$-(polyethylene glycol) or A;

$R_3$ is a linear or branched alkyl group having 1 to 6 carbon atoms or a cyclic alkyl group having 3 to 6 carbon atoms;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

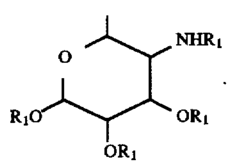

28. The peptide of claim 27, wherein the amino terminus is modified by acetylation.

29. The peptide of claim 27, wherein the carboxyl terminus is modified.

30. The peptide of claim 29, wherein the carboxyl terminus is modified by amidation.

31. The peptide of claim 27, wherein $R_1$ is selected from the group consisting of H, $C_2H_5$ and $CH_2Ph$.

32. The peptide of claim 31, wherein $R_1$ and $R_2$ each are H.

33. A composition of matter, comprising the cytokine restraining peptide of claim 27 and a pharmaceutically acceptable carrier.

34. A method of restraining pathologically elevated cytokine activity in a subject, comprising administering to the subject an effective amount of the cytokine restraining peptide of claim 27.

35. The method of claim 34, wherein the pathologically elevated cytokine activity is due to inflammation.

36. The method of claim 34, wherein the pathologically elevated cytokine activity is due to cachexia.

37. The method of claim 34, wherein the pathologically elevated cytokine activity is due to a patho-immunogenic disease.

38. The method of claim 34, wherein the pathologically elevated cytokine activity is due to adult respiratory distress syndrome.

39. A cytokine restraining peptide having the sequence of (D)Phe-Arg-(D)Trp-$X_3$, wherein $X_3$ is

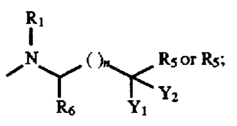

wherein $Y_1$ and $Y_2$ are independently a hydrogen atom, or are taken together to form a carbonyl or thiocarbonyl;

$R_1$ is H, $COCH_3$, $C_2H_5$, $CH_2Ph$, COPh, $COOCH_2Ph$, COO-t-butyl, $CH_2CO$-(polyethylene glycol) or A;

$R_3$ is a linear alkyl group having 1 to 6 carbon atoms or a cyclic alkyl group having 3 to 6 carbon atoms;

$R_5$ is OH, $OR_3$, $NH_2$, SH, $NHCH_3$, $NHCH_2Ph$ or A; and $R_6$ is H or $R_3$;

and wherein "Ph" is $C_6H_5$, "m" is 1, 2 or 3, "n" is 0, 1, 2 or 3, and "A" is a carbohydrate having the general formula:

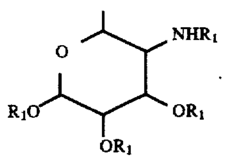

40. The peptide of claim 39, wherein the amino terminus is modified.

41. The peptide of claim 40, wherein the amino terminus is modified by acetylation.

42. The peptide of claim 39, wherein the carboxyl terminus is modified.

43. The peptide of claim 42, wherein the carboxyl terminus is modified by amidation.

44. The peptide of claim 39, wherein $R_1$ is selected from the group consisting of H, $C_2H_5$ and $CH_2Ph$.

45. The peptide of claim 44, wherein $R_1$ and $R_2$ each are H.

46. A composition of matter, comprising the cytokine restraining peptide of claim 39 and a pharmaceutically acceptable carrier.

* * * * *

UNITED STATES PATENT AND TRADEMARK OFFICE

CERTIFICATE OF CORRECTION

PATENT NO. : 5,786,332
DATED : July 28, 1998
INVENTOR(S) : Girten et al.

It is certified that error appears in the above-identified patent and that said Letters Patent is hereby corrected as shown below:

Column 2,
Lines 61 to 65, please delete the structure

" 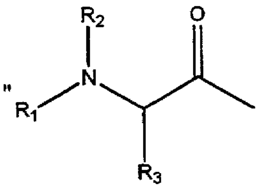 " and replace it with -- 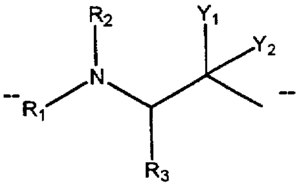 --

Column 3,
Lines 1 to 5, please delete the structure

" 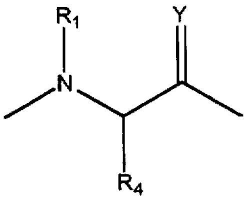 " and replace it with -- 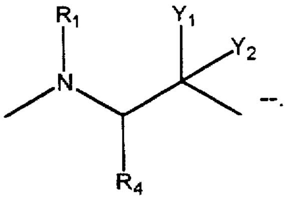 --.

Lines 6 to 10, please delete the structure

" 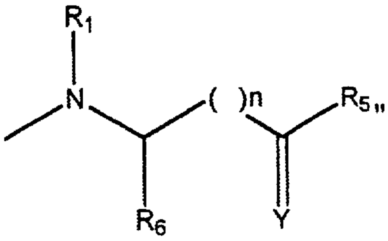 " and replace it with --

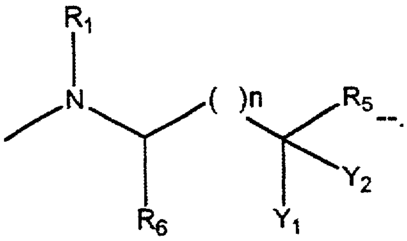 --.

UNITED STATES PATENT AND TRADEMARK OFFICE
CERTIFICATE OF CORRECTION

PATENT NO. : 5,786,332
DATED : July 28, 1998
INVENTOR(S) : Girten et al.

It is certified that error appears in the above-identified patent and that said Letters Patent is hereby corrected as shown below:

Column 3 (continued),
Line 11, please insert -- wherein $Y_1$ and $Y_2$ are independently a hydrogen atom., or are taken together to form a carbonyl of thiocarbonyl; --
Lines 46 to 50, please delete the structure " 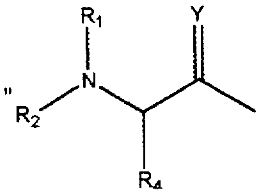 " and replace it with -- 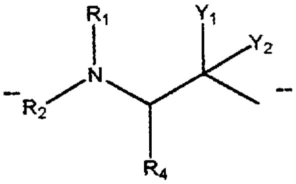 --

Line 52 to 57, please delete the structure

" 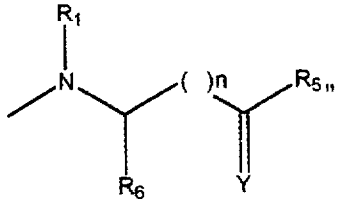 " and replace it with

-- 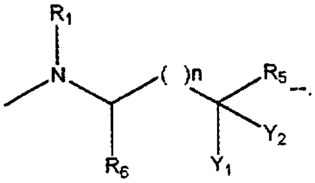 --.

Line 58, please insert -- wherein $Y_1$ and $Y_2$ are independently a hydrogen atom, or are taken together to form a carbonyl of thiocarbonyl; --

Column 5,
Line 5, please delete "*Pentide*" and replace it with -- *Peptide* --

Column 20,
Line 9, please delete "RESPERFUSION" and replace it with -- REPERFUSION --.
Line 17, please delete "as" and replace it with -- was --.

UNITED STATES PATENT AND TRADEMARK OFFICE

CERTIFICATE OF CORRECTION

PATENT NO. : 5,786,332
DATED : July 28, 1998
INVENTOR(S) : Girten et al.

It is certified that error appears in the above-identified patent and that said Letters Patent is hereby corrected as shown below:

Column 25, claim 2,
Line 16, please delete "aroup" and replace it with -- group --.

Column 26, claim 5,
Line 23, please delete "aeneral" and replace it with -- general --.

Column 26, claim 8,
Line 45 to 49, after "$COCH_3$," please insert -- or absent; --.

Signed and Sealed this

Eighth Day of January, 2002

*Attest:*

JAMES E. ROGAN
*Director of the United States Patent and Trademark Office*

*Attesting Officer*